(12) United States Patent
Viola

(10) Patent No.: US 7,497,862 B2
(45) Date of Patent: Mar. 3, 2009

(54) TISSUE MARKING APPARATUS AND METHOD

(75) Inventor: Frank Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 749 days.

(21) Appl. No.: 10/484,119

(22) PCT Filed: Aug. 5, 2002

(86) PCT No.: PCT/US02/25221

§ 371 (c)(1),
(2), (4) Date: Jan. 15, 2004

(87) PCT Pub. No.: WO03/011161

PCT Pub. Date: Feb. 13, 2003

(65) Prior Publication Data

US 2004/0162574 A1   Aug. 19, 2004

Related U.S. Application Data

(60) Provisional application No. 60/309,821, filed on Aug. 3, 2001.

(51) Int. Cl.
*A61B 17/00* (2006.01)
(52) U.S. Cl. .............................. 606/116; 600/7; 604/63
(58) Field of Classification Search ................. 606/116, 606/186, 181, 182, 183, 184, 185; 604/59, 604/60, 61, 62, 63, 64, 57; 600/3, 4, 7, 8
See application file for complete search history.

(56) References Cited

U.S. PATENT DOCUMENTS

| | | | |
|---|---|---|---|
| 67,545 A | 8/1867 | Hodgins | |
| 1,406,509 A * | 2/1922 | Viol | 600/7 |
| 1,868,308 A * | 7/1932 | Brumfield | 604/59 |
| 2,007,626 A * | 7/1935 | Waring | 604/59 |
| 2,017,783 A * | 10/1935 | Clark | 604/63 |
| 2,907,327 A * | 10/1959 | White | 604/60 |
| 3,173,414 A | 3/1965 | Guillant | |
| 3,561,429 A | 2/1971 | Jewett | |
| 3,683,891 A | 8/1972 | Eokridge et al. | |
| 3,858,783 A | 1/1975 | Kapitanov et al. | |
| 4,011,873 A | 3/1977 | Hoffmeister | |

(Continued)

FOREIGN PATENT DOCUMENTS

SU   596232   3/1978

(Continued)

*Primary Examiner*—Darwin P Erezo

(57) ABSTRACT

Tissue marking apparatus for marking a tissue mass of interest within the body of a patient are disclosed. The tissue marking apparatus include a handle, a tube operatively coupled to a distal end of the handle, a push rod disposed within the tube and extending into the handle, a firing mechanism retained within the handle and operatively coupled to a proximal end of the push rod, and a potential energy source configured and adapted to rapidly drive the push rod distally through the tube upon an activation of the firing mechanism. The tissue marking apparatus further includes a marker configured and dimensioned to be slidably received within the tube at a location distal of the push rod. The marker includes a capsule defining a chamber therein, an elongate tail extending from a distal end thereof, and at least one radioactive bead retained within the chamber of the capsule.

5 Claims, 15 Drawing Sheets

U.S. PATENT DOCUMENTS

| | | | |
|---|---|---|---|
| 4,445,517 A | | 5/1984 | Field |
| 4,474,308 A | * | 10/1984 | Bergeron ..................... 221/24 |
| 4,588,395 A | * | 5/1986 | Lemelson ................... 604/59 |
| 4,595,007 A | | 6/1986 | Mericle |
| 4,616,656 A | | 10/1986 | Nicholson et al. |
| 4,790,329 A | | 12/1988 | Simon |
| 4,795,458 A | | 1/1989 | Regan |
| 4,799,495 A | | 1/1989 | Hawkins et al. |
| 4,846,793 A | * | 7/1989 | Leonard et al. ............... 604/62 |
| 4,869,259 A | | 9/1989 | Elkins |
| 4,915,686 A | * | 4/1990 | Frederick ..................... 604/60 |
| 4,925,445 A | | 5/1990 | Sakamoto et al. |
| 4,932,962 A | | 6/1990 | Yoon et al. |
| 4,957,476 A | * | 9/1990 | Cano ............................. 600/7 |
| 4,990,136 A | * | 2/1991 | Geria ........................... 604/63 |
| 4,994,028 A | * | 2/1991 | Leonard et al. ............... 604/60 |
| 5,002,548 A | * | 3/1991 | Campbell et al. ........... 606/116 |
| 5,018,530 A | | 5/1991 | Rank et al. |
| 5,053,047 A | | 10/1991 | Yoon |
| 5,122,136 A | | 6/1992 | Guglielmi et al. |
| 5,135,493 A | * | 8/1992 | Peschke ........................ 604/61 |
| 5,147,295 A | * | 9/1992 | Stewart ........................ 604/61 |
| 5,197,484 A | | 3/1993 | Kornberg et al. |
| 5,220,928 A | | 6/1993 | Oddsen et al. |
| 5,221,269 A | | 6/1993 | Miller et al. |
| 5,222,976 A | | 6/1993 | Yoon |
| 5,258,000 A | | 11/1993 | Gianturco |
| 5,284,479 A | * | 2/1994 | de Jong ........................ 604/60 |
| 5,292,326 A | | 3/1994 | Green et al. |
| 5,330,503 A | | 7/1994 | Yoon |
| 5,350,392 A | * | 9/1994 | Purcell et al. ............... 606/182 |
| 5,389,102 A | | 2/1995 | Green et al. |
| 5,405,321 A | | 4/1995 | Reeves |
| 5,423,856 A | | 6/1995 | Green |
| 5,433,739 A | | 7/1995 | Sluijter et al. |
| 5,437,166 A | | 8/1995 | Gardner |
| 5,489,287 A | | 2/1996 | Green et al. |
| 5,498,227 A | | 3/1996 | Mawad |
| 5,511,556 A | | 4/1996 | DeSantis |
| 5,522,797 A | * | 6/1996 | Grimm ........................ 604/61 |
| 5,526,822 A | | 6/1996 | Burbank et al. |
| 5,531,761 A | | 7/1996 | Yoon |
| 5,560,373 A | | 10/1996 | DeSantis |
| 5,562,685 A | | 10/1996 | Mollenauer et al. |
| 5,573,541 A | | 11/1996 | Green et al. |
| 5,582,616 A | | 12/1996 | Bolduc et al. |
| 5,607,467 A | | 3/1997 | Froix |
| 5,709,692 A | | 1/1998 | Mollenauer et al. |
| 5,772,671 A | | 6/1998 | Harmon |
| 5,782,775 A | | 7/1998 | Milliman et al. |
| 5,782,844 A | | 7/1998 | Yoon et al. |
| 5,800,445 A | | 9/1998 | Ratcliff et al. |
| 5,810,769 A | | 9/1998 | Schlegel et al. |
| 5,810,822 A | | 9/1998 | Mortier |
| 5,810,851 A | | 9/1998 | Yoon |
| 5,824,008 A | | 10/1998 | Boldvc et al. |
| 5,830,221 A | | 11/1998 | Stein et al. |
| 5,853,366 A | | 12/1998 | Dowlatshahi |
| 5,879,357 A | | 3/1999 | Heaton et al. |
| 5,906,573 A | | 5/1999 | Aretz |
| 5,924,973 A | | 7/1999 | Weinberger |
| 5,928,130 A | | 7/1999 | Schmidt |
| 5,961,457 A | | 10/1999 | Raylman et al. |
| 5,961,458 A | | 10/1999 | Carroll |
| 5,989,265 A | | 11/1999 | Bouquet DeLa Jolinrere et al. |
| 6,007,475 A | * | 12/1999 | Slater et al. ..................... 600/8 |
| 6,024,690 A | | 2/2000 | Lee et al. |
| 6,030,333 A | | 2/2000 | Sioshansi et al. |
| 6,056,686 A | | 5/2000 | Mawad |
| 6,077,231 A | | 6/2000 | Milliman et al. |
| 6,080,099 A | * | 6/2000 | Slater et al. ..................... 600/8 |
| 6,095,967 A | * | 8/2000 | Black et al. ..................... 600/7 |
| 6,099,458 A | * | 8/2000 | Robertson ....................... 600/8 |
| 6,102,844 A | * | 8/2000 | Ravins et al. ................... 600/8 |
| 6,142,955 A | | 11/2000 | Farascioni et al. |
| 6,161,034 A | | 12/2000 | Burbank et al. |
| 6,165,137 A | | 12/2000 | Milliman et al. |
| 6,175,760 B1 | | 1/2001 | Baskin et al. |
| 6,228,055 B1 | | 5/2001 | Foerster et al. |
| 6,496,717 B2 | | 12/2002 | Cox et al. |
| 6,505,392 B1 | * | 1/2003 | Liprie .......................... 29/460 |
| 6,554,760 B2 | * | 4/2003 | Lamoureux et al. ............ 600/7 |
| 6,876,712 B1 | * | 4/2005 | Liprie ........................ 376/158 |
| 2002/0087078 A1 | | 7/2002 | Cox et al. |
| 2003/0092985 A1 | | 5/2003 | Cox et al. |

FOREIGN PATENT DOCUMENTS

| | | |
|---|---|---|
| SU | 652940 | 3/1979 |
| SU | 915844 | 3/1982 |

* cited by examiner

Dense/Fatty

Dense/Fatty

As fired in a mix of dense and fatty tissue

In air, or as fired in soft/fatty tissue

TISSUE MARKING APPARATUS AND METHOD

CROSS-REFERENCE TO RELATED APPLICATIONS

The present application claims priority of U.S. Provisional Patent Application Ser. No. 60/309,821, filed Aug. 3, 2001, the entire contents of which are incorporated herein by reference.

BACKGROUND

1. Technical Field

The present disclosure relates to a tissue marking apparatus and method and, more particularly, to an apparatus and method for marking suspect tissue for repeated monitoring over time.

2. Background of Related Art

Interstitial medical diagnosis and treatment require means for effectively marking a tissue mass of interest, such as a tumor, lesion, cyst or similar tissue disorder. Marking has traditionally been accomplished using an elongate wire having a barbed or similar engaging end. The elongate wire is configured to be inserted such that the barbed end penetrates the subject tissue mass with the opposite end of the elongate wire extending out from the body so as to be visible upon inspection. In this manner, the elongate wire provides a path for subsequent incision and allows for easy removal of the wire once diagnosis and treatment are complete.

Significant developments in the localization and demarcation of tissue, bearing radioactive isotope tags for diagnostic and/or therapeutic purposes has occurred over the years. For example, monoclonal antibodies or other tumor or lymph node localizing agents, tagged with a radioactive isotope (e.g., Technetium 99 m, Indium 111, Iodine 123 and Iodine 125), have been introduced into the body of a patient in order to diagnose and/or treat certain diseases, e.g., cancer. Such radiopharmaceuticals tend to localize in particular tissue, such as the cancerous tissue, so that the gamma radiation emitted by the isotope agent can be detected by a radiation detector, e.g., a probe. In particular, the radiation detector or probe is disposed or positioned adjacent a portion of the patient's body where the cancerous tissue is suspected to be in order to detect if any radiation is emanating from that site. If it is, this indicates that cancerous tissue is likely to be found at this site.

Additionally, invasive surgical techniques have been employed to implant markers directly into the patient's body. For example, during a coronary artery bypass graft (CABG), which constitutes open heart surgery, it is common practice to surgically apply one or more metallic rings to the aorta at the site of the graft. This enables a practitioner to later return to the site of the graft by identifying the rings, for evaluative purposes. It is also common practice to mark a surgical site with staples, vascular clips and the like for the purpose of future evaluation of the site.

Accordingly, the need exists for apparatus and methods of non-surgically implanting potentially permanent markers at the situs of the tumor or other tissue mass of interest, for the purpose of defining the margins of the tumor before it is removed and/or to establish its location after it has been removed. Preferably, the markers should be easy to deploy and easy to detect using state of the art imaging techniques.

SUMMARY

The present disclosure is directed to apparatus used for marking a tissue mass of interest within the body of a patient. The present disclosure is also directed to methods of using the apparatus of the present disclosure to mark the tissue mass.

In accordance with the present disclosure, a tissue marking apparatus, for marking a tissue mass of interest within the body of a patient, includes a handle, a tube operatively coupled to a distal end of the handle, a push rod disposed within the tube and extending into the handle and a firing mechanism retained within the handle and operatively coupled to a proximal end of the push rod. The firing mechanism is configured and adapted to distally advance the push rod through the tube.

The tissue marking apparatus preferably includes a marker configured and dimensioned to be slidably received within the tube at a location distal of the push rod. Preferably, the marker includes a capsule defining a chamber therein, an elongate tail extending from a distal end thereof, and at least one radioactive bead retained within the chamber of the capsule. The elongate tail preferably has a hoop shape in an at rest condition and is deformable to a substantially linear condition. It is contemplated that the elongate tail can have an elliptical, triangular, square, rectangular or polygonal shape while in the at rest condition.

In an embodiment, the capsule of the marker includes a distal capsule portion from which the elongate tail extends and a proximal capsule portion having a chamber formed therein for retaining the at least one radioactive bead. The distal and proximal capsule portions are preferably configured and adapted to be secured to one another and to house the at least one radioactive bead within the chamber thereof.

Preferably, the firing mechanism includes a potential energy source configured and adapted to rapidly drive the push rod distally through the tube upon an activation of the firing mechanism.

In one embodiment, the firing mechanism includes a piston slidably retained within the handle, a compression spring slidably disposed between the piston and an inner proximal surface of the handle, an eccentric rod having a proximal end securely retained within the piston and a distal end selectively retained within a detent formed in a distal surface of the handle, and a firing button operatively coupled to the handle. The eccentric rod presses the piston against the spring in order to maintain the spring in a compressed condition. The firing button is configured and adapted to disengage the distal end of the eccentric rod from the detent to permit the spring to decompress.

In an alternative embodiment, the firing mechanism includes a compression spring slidably retained within the handle and a firing button slidably retained within the handle. The firing button includes a distal end defining a piston, a proximal end defining a lip configured and adapted to engage an edge of an opening formed in a proximal end of the handle, and a shaft portion interconnecting the distal and proximal ends of the firing button. The shaft portion and the proximal end of the firing button preferably extend through the compression spring such that the compression spring is disposed between the piston and the proximal end of the handle. In use, when the lip of the firing button is engaged with the edge of the opening formed in the proximal end of the handle, the compression spring is maintained in a compressed condition.

The tissue marking apparatus can further include a locking tab configured and adapted to prevent the manipulation of the firing mechanism. The locking tab is preferably inserted within the opening formed in the proximal end of the handle, between the proximal end of the firing button and a lower edge of the opening formed in the proximal end of the handle. The locking tab prevents the lip at the proximal end of the firing button from disengaging from the edge of the opening formed in the proximal end of the handle and thereby inadvertently firing.

The handle of the tissue marking apparatus preferably includes a distal body portion from which the tube extends and a proximal body portion. The distal and proximal body portions are preferably couplable with one another.

A marker, for use with a tissue marking apparatus disclosed herein, can include a capsule, an elongate tail extending from the capsule, and at least one radioactive bead retained within the capsule.

Preferably, the capsule includes a distal capsule portion from which the elongate tail extends and a proximal capsule portion defining a chamber therein. The distal capsule portion and the proximal capsule portion are configured and adapted to be secured to one another and to house the at least one radiation bead within the chamber thereof.

Preferably, the elongate tail has a hoop shape while in an at rest condition and is deformable to a substantially linear condition. The elongate tail can be made of a shape memory alloy.

The present disclosure also provides a method of marking a biological tissue site within the body of a patient. The method includes the steps of inserting a tissue marking apparatus, having a tissue marker loaded therein, into a desired location of the patient, firing the tissue marking apparatus such that the tissue marker is ejected from the tissue marking apparatus and at least partially embedded in the body of the patient, and withdrawing the tissue marking apparatus from the body of the patient. Preferably, the tissue marker remains wholly within the body of the patient and is positioned proximate the desired location.

Preferably, the tissue marking apparatus includes a handle, a tube operatively coupled to a distal end of the handle, a push rod disposed within the tube and extending into the handle, a firing mechanism retained within the handle and operatively coupled to a proximal end of the push rod, and a potential energy source configured and adapted to rapidly drive the push rod distally through the tube upon an activation of the firing mechanism. The firing mechanism is preferably configured and adapted to distally advance the push rod through the tube and fire at least one marker into the body of the patient.

The marker preferably includes a capsule having a distal capsule portion from which the elongate tail extends and a proximal capsule portion having a chamber formed therein, an elongate tail extending from the distal capsule portion, and at least one radioactive bead retained within the chamber of the proximal capsule portion. The tail preferably has a hoop shape while in an at rest condition and is deformable to a substantially linear condition.

In one embodiment, the firing mechanism includes a piston slidably retained within the handle, a compression spring slidably disposed within the handle, an eccentric rod having a proximal end securely retained within the piston and a distal end selectively retained within a detent formed in a proximal surface of the handle, and a firing button operatively coupled to the handle, the firing button being configured and adapted to disengage the distal end of the eccentric rod from the detent to permit the spring to decompress. The eccentric rod preferably presses the piston against the spring to maintain the spring in a compressed condition.

In an alternative embodiment, the firing mechanism includes a compression spring slidably retained within the handle and a firing button slidably retained within the handle. The firing button preferably includes a distal end defining a piston, a proximal end defining a lip configured and adapted to engage an edge of an opening formed in a proximal end of the handle, and a shaft portion interconnecting the distal and proximal ends of the firing button. The shaft portion and the proximal end of the firing button preferably extend through the compression spring such that the compression spring is disposed between the distal end of the firing button and the proximal end of the handle. The compression spring is preferably maintained in a compressed condition when the lip of the firing button is engaged with the edge of the opening formed in the proximal end of the handle.

Other advantages and features of the apparatus and method disclosed herein will become apparent from the following description of preferred embodiments, the accompanying drawings and the claims.

BRIEF DESCRIPTION OF THE DRAWINGS

The accompanying drawings, which are incorporated in and constitute a part of this specification, illustrate the preferred embodiments, and together with the description, serve to explain the principles of the presently disclosed apparatus, wherein.

DETAILED DESCRIPTION OF PREFERRED EMBODIMENTS

Figure 1:
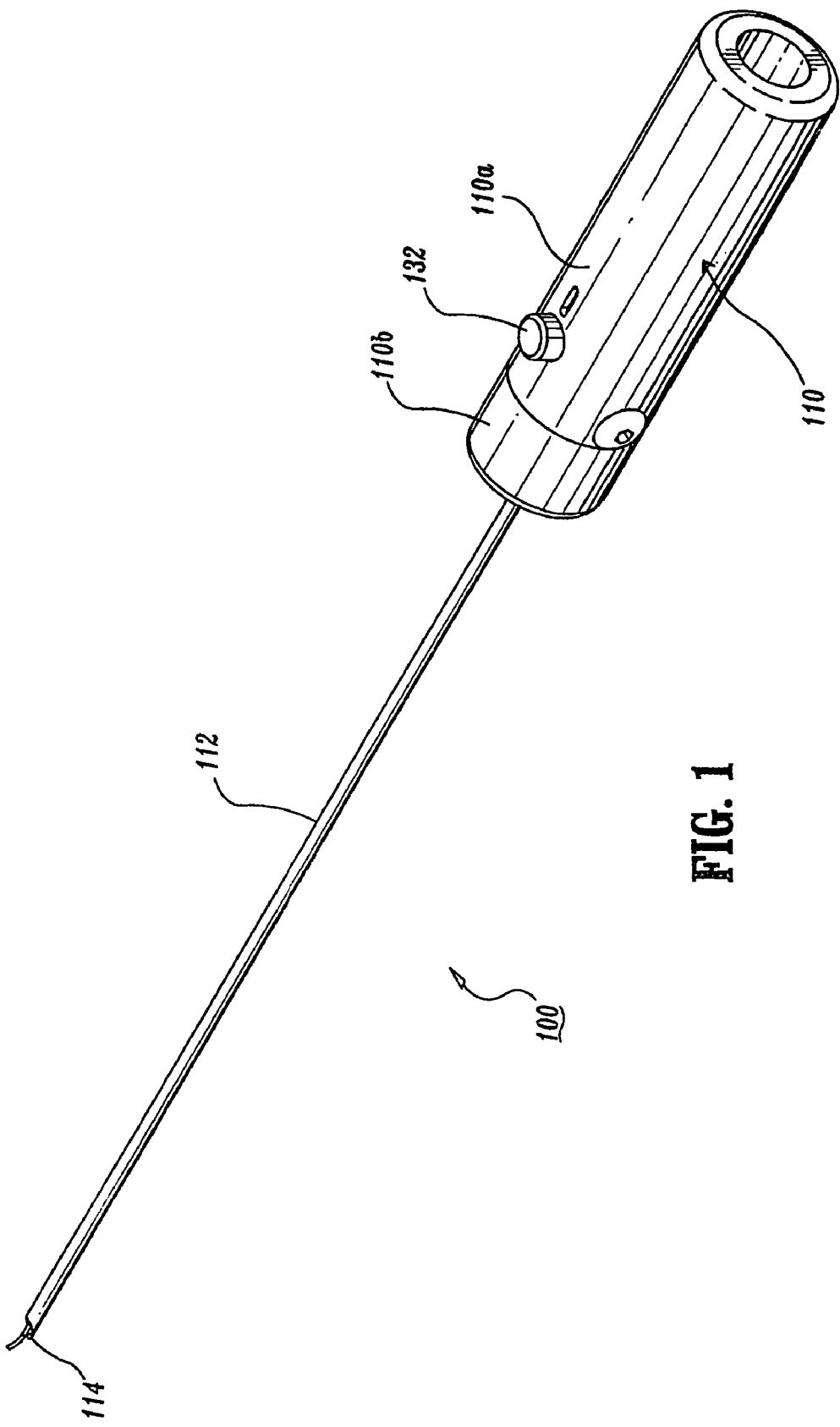
FIG. 1 is a perspective view of a tissue marking apparatus constructed in accordance with one illustrative embodiment of the present disclosure.

Preferred embodiments of the presently disclosed target marking apparatus will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Figure 2:
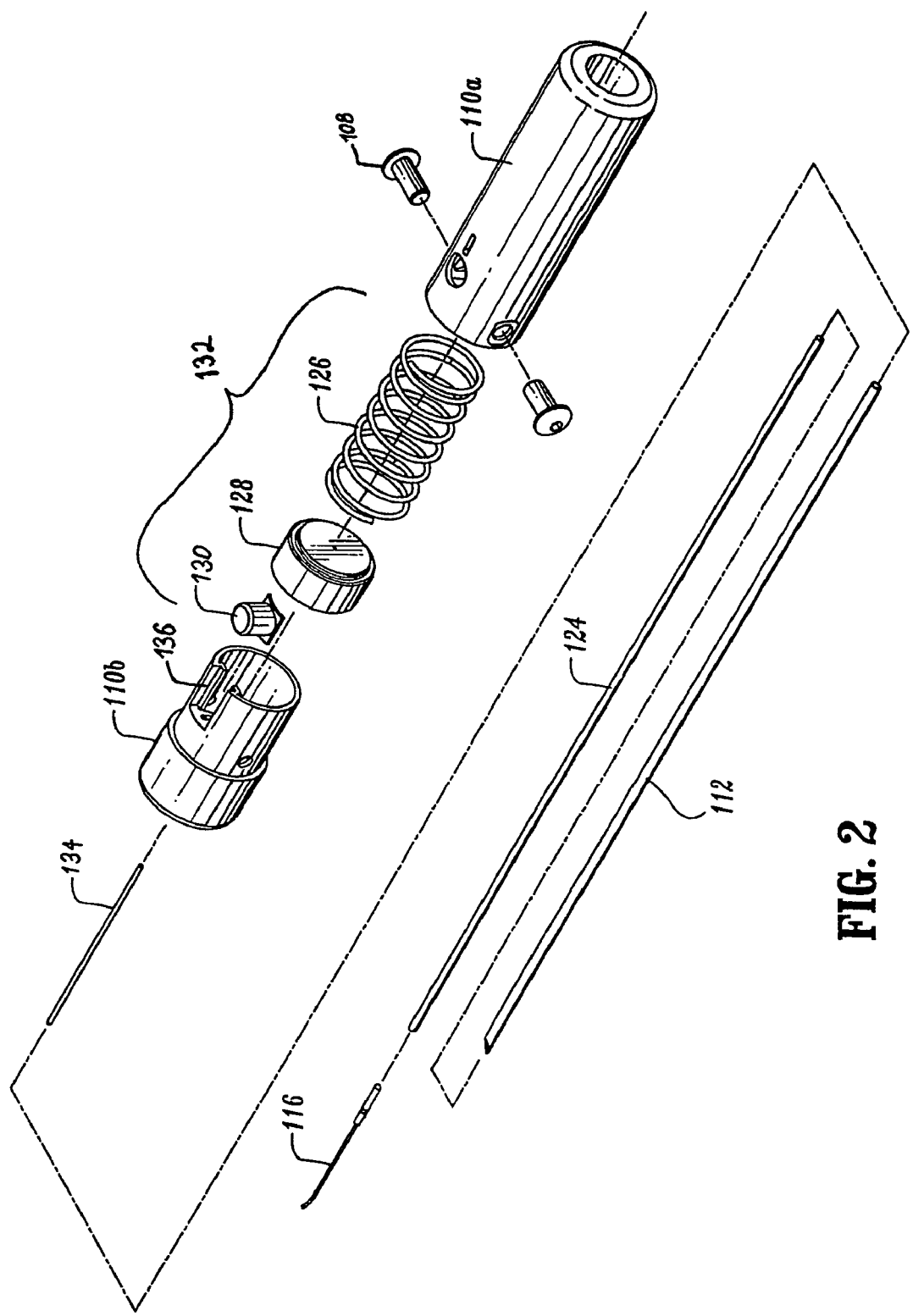
FIG. 2 is a perspective view, with parts separated, of the tissue marking apparatus of FIG. 1.
Figure 2A:
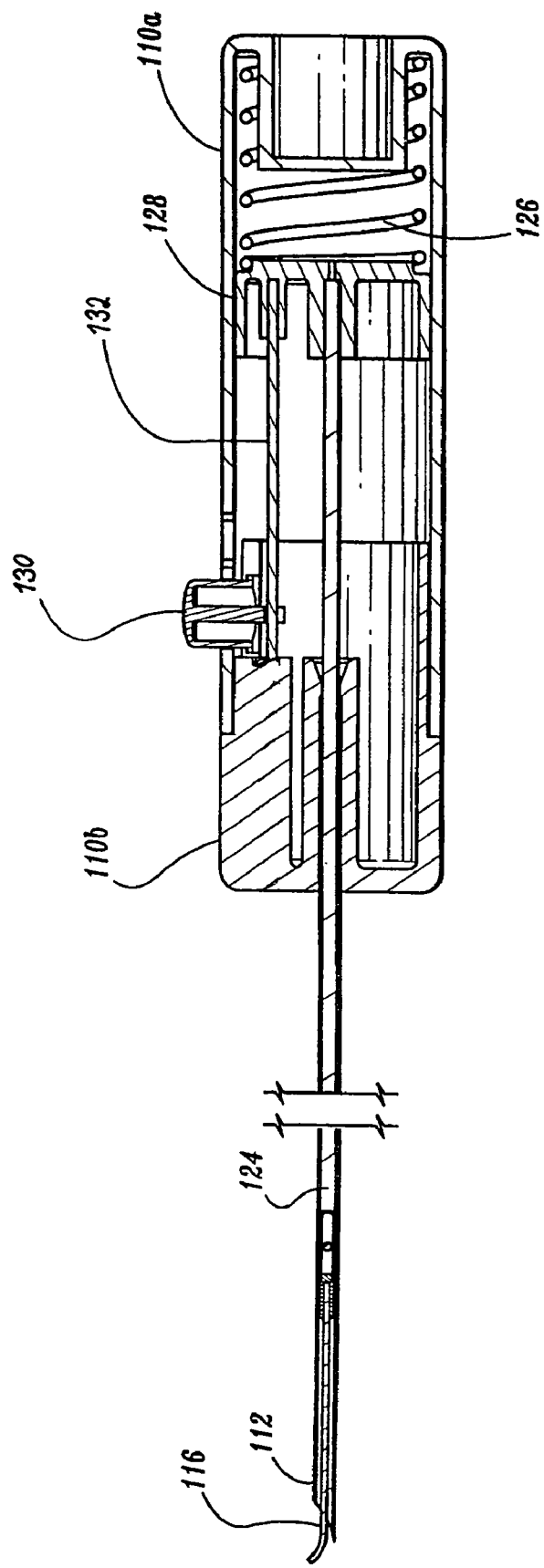
FIG. 2A is a cross-sectional side elevational view, taken along the longitudinal axis, of the tissue marking apparatus of FIG. 1.

Referring now in specific detail to the drawings, in which like referenced numerals identify similar or identical elements throughout the several views and initially to FIGS. 1, 2 and 2A, a preferred embodiment of a tissue marking apparatus is generally disclosed as 100. Tissue marking apparatus 100 includes a barrel shaped handle 110 having a hollow proximal barrel portion 100a and a hollow distal barrel portion 110b which are secured together by suitable fastening techniques. Tissue marking apparatus 100 further includes an elongated outer tube 112 extending from distal barrel portion 110b. Preferably, outer tube 112 is formed of stainless steel or other suitable material for insertion into tissue of a patient. To facilitate insertion through the patient's skin to the target tissue, outer tube 112 is provided with a beveled/sharpened distal tip 114. As seen in FIG. 2, distal barrel portion 110b can include a region of reduced diameter which is sized to be received within proximal hollow barrel portion 110a. Accordingly, at least one fastening element 108 (i.e., a screw) can be provided which extends through proximal barrel portion 110a and into distal barrel portion 110b in order to secure proximal barrel portion 110a to distal barrel portion 110b.

Tissue marking apparatus 100 further includes a push rod 124 disposed within outer tube 112. Handle 110 houses a firing mechanism 132 adapted to rapidly deploy tissue marker 116 from the distal end of outer tube 112. Firing mechanism 132 includes, for example, a potential energy storage and release mechanism, such as a coil spring 126. Coil spring 126 of firing mechanism 132 is configured and dimensioned to be slidingly retained within handle 110. Firing mechanism 132 further includes a piston element 128 slidably positioned within distal and proximal barrel portions 110a, 110b and distal of spring 126 which is retained within handle 110. Piston element 128 is configured and adapted to securely receive a proximal end of push rod 124 in a distal end thereof, as seen in FIG. 2A.

Firing mechanism also includes a firing button 130, disposed in a slot 136 formed in distal barrel portion 110b, which is in radial alignment with an eccentric rod 134. Eccentric rod 134 has a proximal end which is press fit into a receiving feature formed on the distal surface of piston element 128 and a distal end which engages a detent formed in a surface of distal barrel portion 110b. Eccentric rod 134 is provided in order to maintain spring 126 in a compressed condition thereby preventing distal movement of piston element 128.

Turning to FIGS. 9-13, a tissue marker 116, constructed in accordance with the present disclosure, is configured and adapted to be disposed in the distal end of outer tube 112 of tissue marking apparatus 100. Tissue marker 116 includes a capsule 118 and a flexible elongate tail 120 extending from the distal end thereof. Capsule 118 is preferably formed of two portions, a distal portion and a proximal portion 118a, 118b, respectively, which are configured and dimensioned to receive one or more radioactive beads 122 within a hollow interior chamber 119 formed therebetween. Preferably, distal and proximal portions 118a, 118b of capsule 118 can be sealed closed in order to prevent beads 122 from escaping therefrom. Distal portion 118a of capsule 118 is secured to the proximal end of elongated tail 120 while proximal portion 118b of capsule 118, having at least one bead 122 contained in hollow chamber 119 thereof, is secured to distal portion 118a. Preferably, capsule 118 is made from a biocompatible material, such as, for example, stainless steel, titanium and certain plastics known by those of skill in the art.

Elongated tail 120 of marker 116 is preferably formed from a super-elastic metal having a substantially hoop-like shape while in an at rest condition. The elongate tail 120 is capable of being deformed to a substantially straightened configuration to fit in the distal end of outer tube 112. Alternatively, elongate tail 120 can be constructed from a shape memory alloy. While a hoop-like shape for elongate tail 120 is depicted and described, it is envisioned that elongate tail 120 can be non-circular, such as, for example, elliptical, triangular, square, rectangular or polygonal. In other words, a distal end of elongate tail 120, while in an at rest condition, will have a tendency to wrap around and approach a median portion of elongate tail 120.

As best seen in FIG. 2A, upon assembly, spring 126 is compressed and eccentric flexible rod 134 is positioned between piston element 128 and distal barrel portion 110b such that eccentric flexible rod 134 is in radial alignment with firing button 130 which is disposed in slot 136 of distal barrel portion 110b. A tissue marker 116 is disposed within outer tube 112 at a location distal of push rob 124. In this manner, upon pushing firing button 130, eccentric rod 134 is forced out of the detent formed in distal barrel portion 110b and out of axial alignment thereby permitting rapid decompression of spring 126 and consequent distal movement of piston element 128 to urge push rod 124 forward and to force tissue marker 116 out from the distal end of outer tube 112 with sufficient velocity to penetrate the surrounding tissue without pushing the surrounding tissue out of the way.

Figure 3:
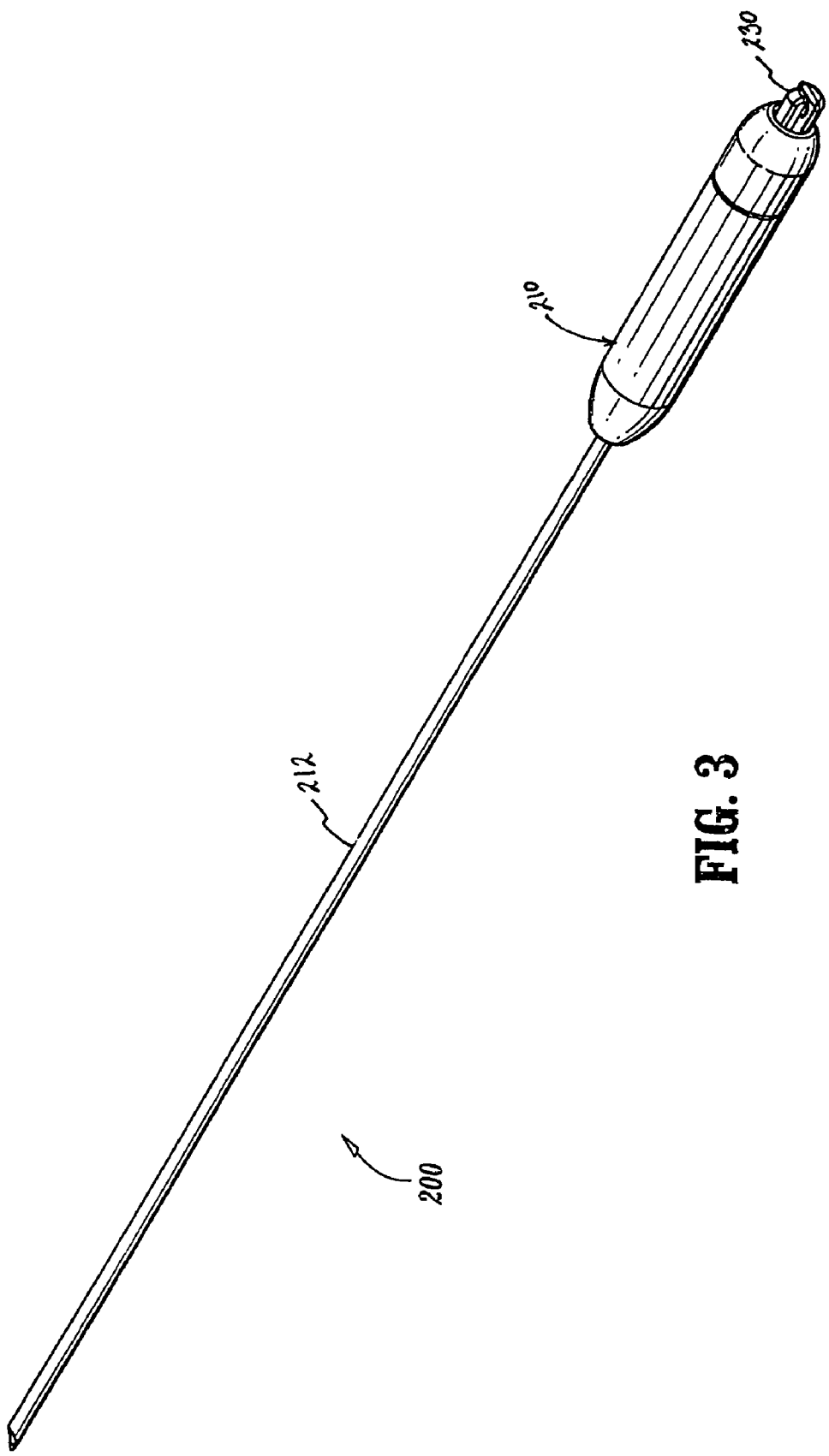
FIG. 3 is a perspective view of a tissue marking apparatus constructed in accordance with another embodiment of the present disclosure.
Figure 4:
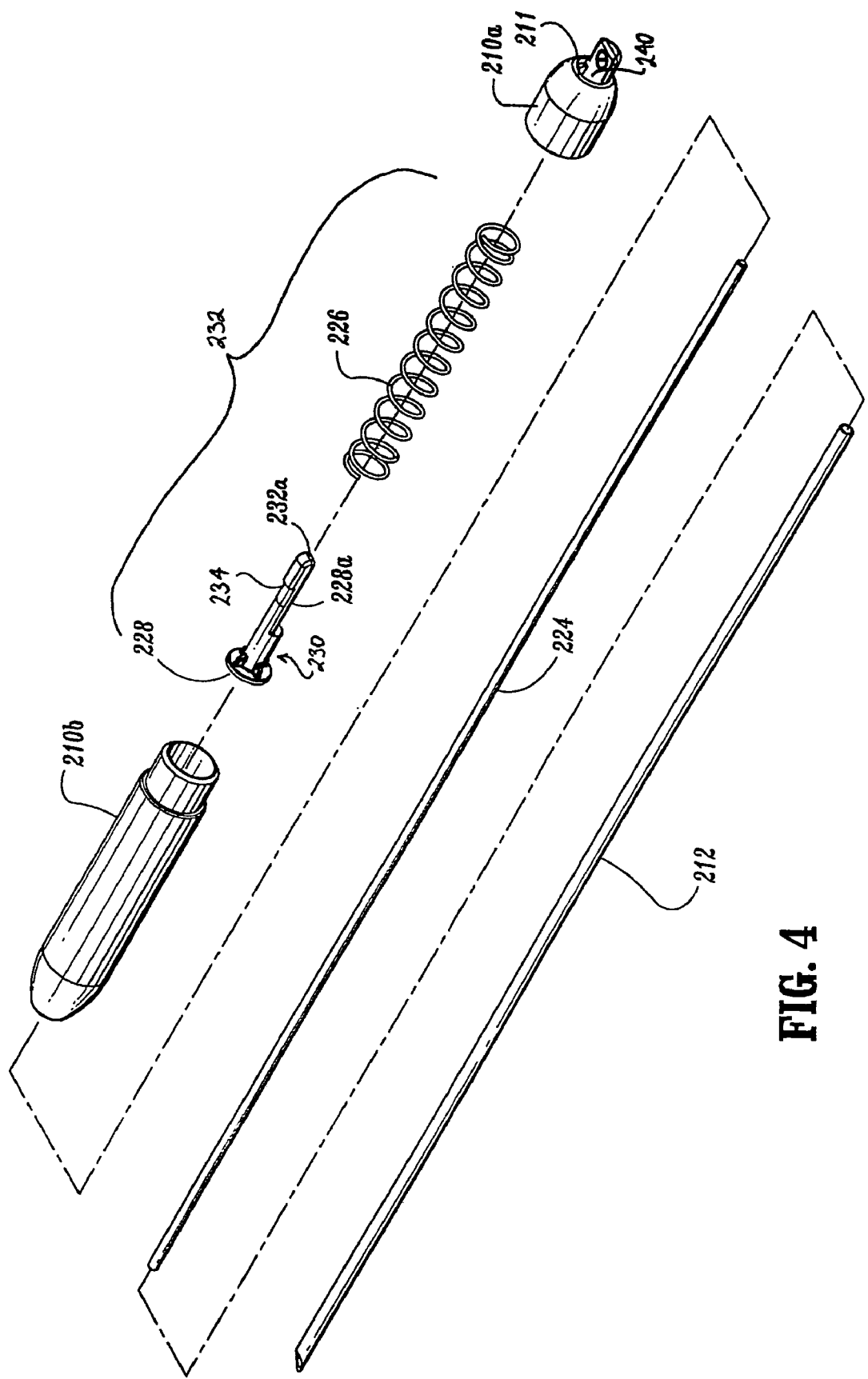
FIG. 4 is a perspective view, with parts separated, of the tissue marking apparatus of FIG. 3.
Figure 4A:
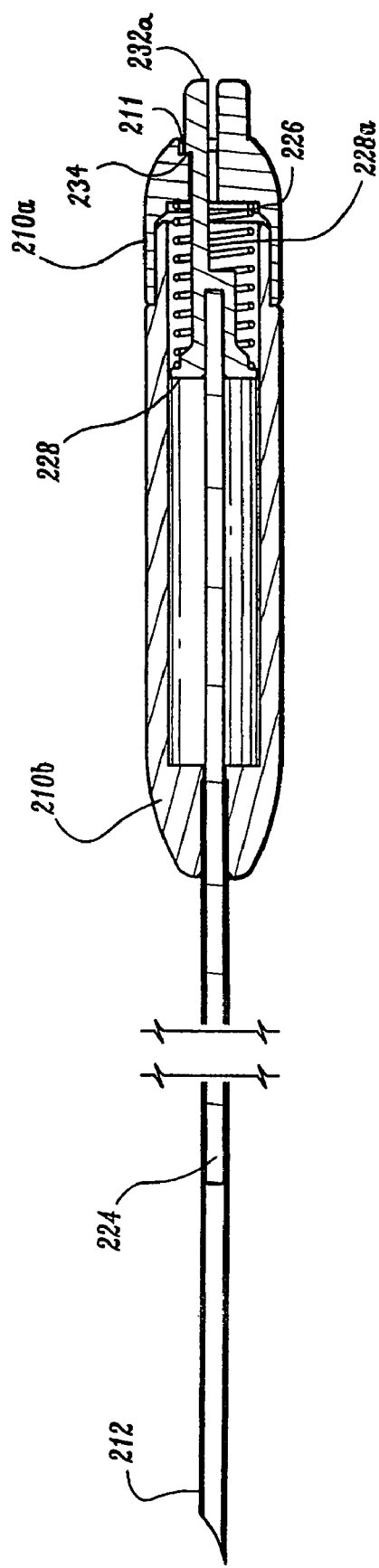
FIG. 4A is a cross-sectional side elevational view, taken along the longitudinal axis, of the tissue marking apparatus of FIG. 3.
Figure 5:
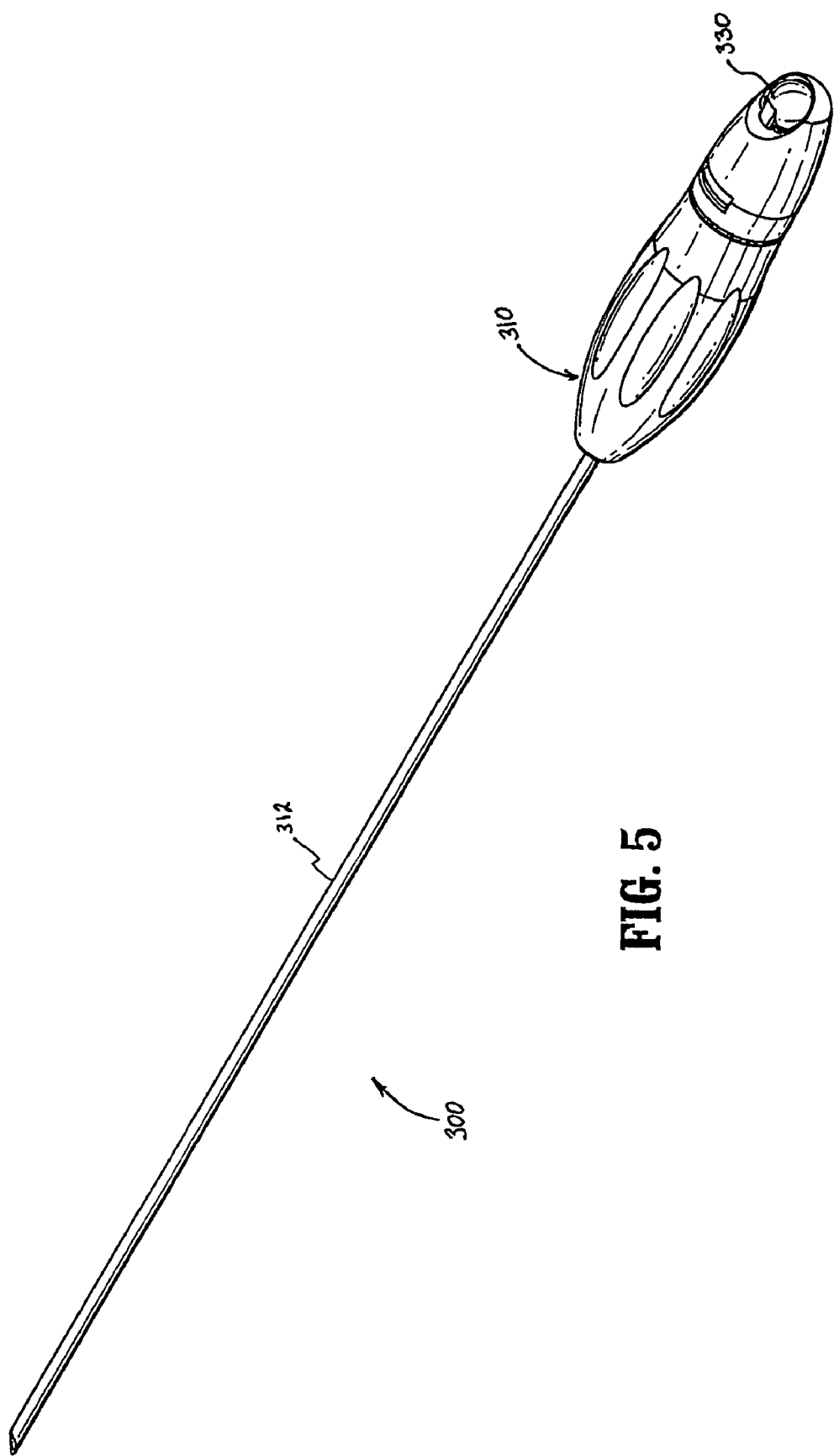
FIG. 5 is a perspective view of a tissue marking apparatus constructed in accordance with a further embodiment of the present disclosure.
Figure 7:
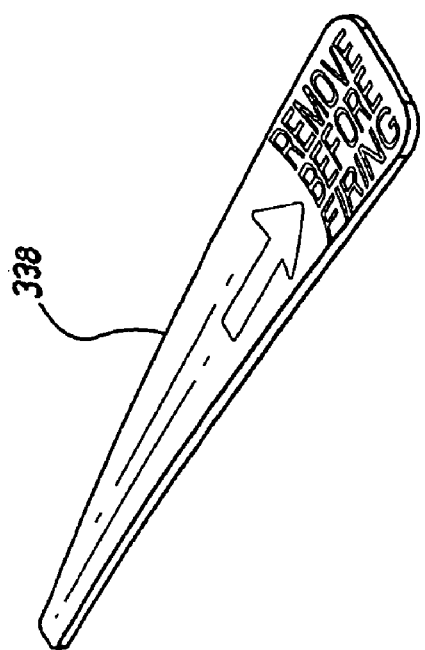
FIG. 7 is an enlarged perspective view of the firing safety tab of FIG. 6.
Figure 6:
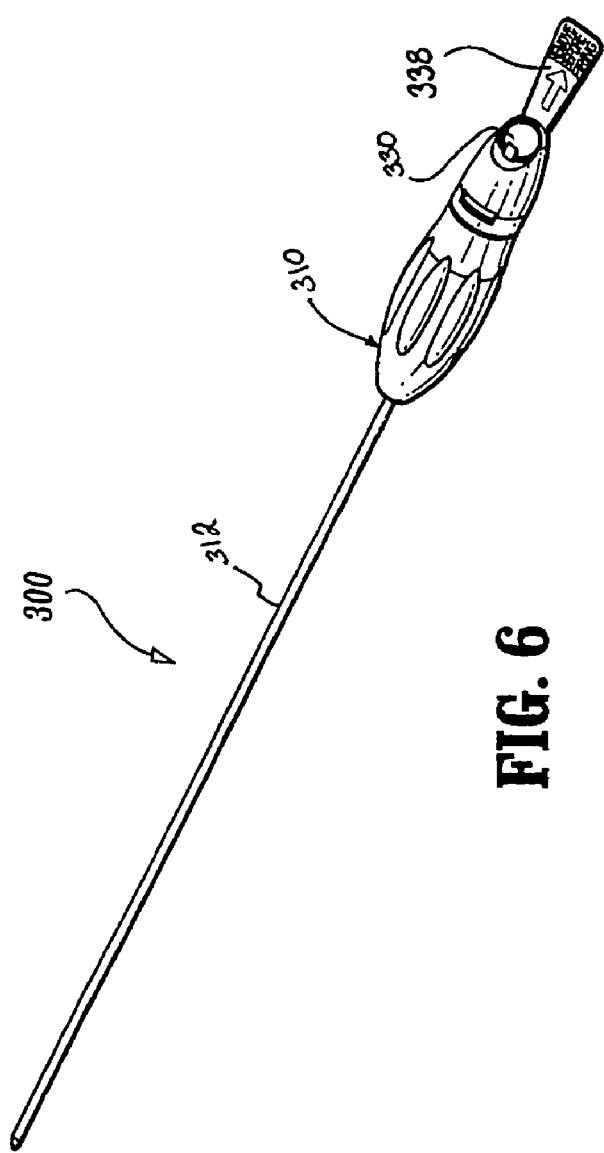
FIG. 6 is a perspective view of the tissue marking apparatus of FIG. 5 with a firing safety tab in place.

Referring now to FIGS. 3, 4 and 4A, a further embodiment of a tissue marking apparatus is generally shown as 200. Tissue marking apparatus 200 includes a hollow tubular shaped handle 210 having a proximal tubular portion 210a and a distal tubular portion 210b which are secured together by suitable fastening techniques. An elongated outer tube 212 extends from distal portion 210b.

Tissue marking apparatus 200 further includes a push rod 224 disposed within outer tube 212, immediately proximal of a tissue marker 116 (as described above), to facilitate deployment of marker 116 from outer tube 212. Handle 210 houses a firing mechanism 232 adapted to rapidly deploy tissue marker 116 from the distal end of outer tube 212. Firing mechanism 232 includes a coil spring 226 configured and dimensioned to be slidably received within proximal and distal tubular portions 210a, 210b. Firing mechanism 232 further includes a firing button 230 having a piston element 228 at a distal end thereof, a ledge surface 232a at a proximal end thereof and a shaft portion 228a interconnecting piston element 228 and ledge surface 232a Piston element 228 is preferably configured and adapted to securely receive a proximal end of push rod 124 in a distal end thereof, as seen in FIG. 4A. Preferably, ledge surface 232a defines a shoulder 234, which shoulder 234 serves to retain spring 226 in a compressed state, between piston element 228 and a distal surface of proximal tubular portion 210a, when ledge surface 232a extends through a longitudinal opening 240 formed through proximal tubular portion 210a and engages arcuate surface 211 of longitudinal opening 240 in a snap-fit type engagement, as seen in FIG. 4A.

In this manner, upon squeezing or depressing ledge surface 232a, thereby disengaging shoulder 234 from arcuate surface 211, spring 226 is rapidly decompressed, thereby pressing against the proximal surface of piston element 228, resulting in consequent distal movement of piston element 228 to urge push rod 224 forward and to force tissue marker 116 out from the distal end of outer tube 212. Accordingly, tissue marker 116 is expelled with sufficient velocity to penetrate the surrounding tissue without pushing the surrounding tissue out of the way.

Referring now to FIGS. 5-8A, a tissue marking apparatus, in accordance with a further alternative embodiment of the present disclosure, for deploying a tissue marker 116, is shown generally as 300. Tissue marking apparatus 300 includes a hollow tubular shaped handle 310 having a proximal tubular portion 310a and a distal tubular portion 310b which are secured together by suitable fastening techniques, such as, for example, a recess 308a formed in proximal tubular portion 310a which is configured and dimensioned to receive a radial projection 308b extending from distal tubular portion 310b in a snap-fit type engagement.

Figure 8:
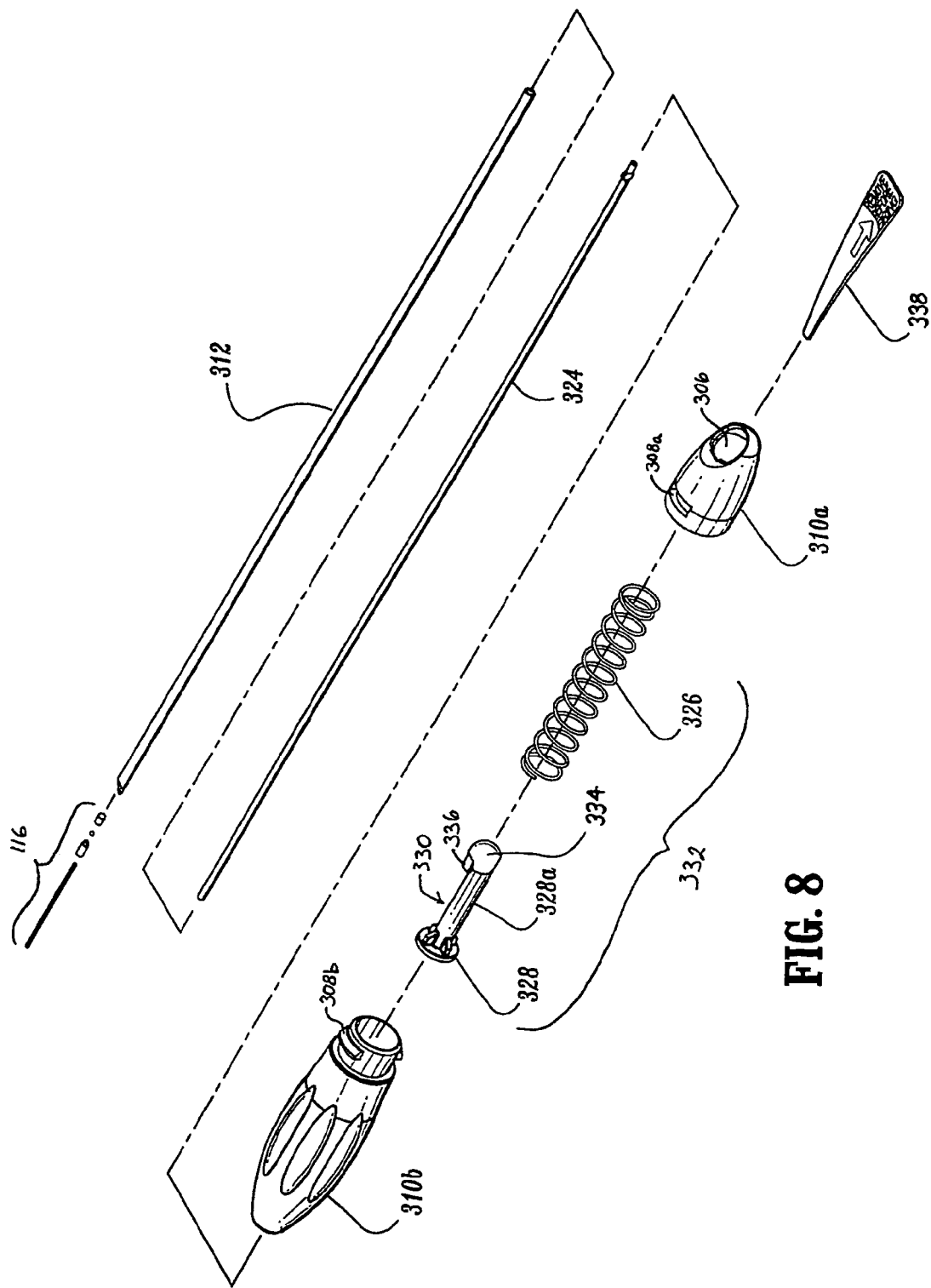
FIG. 8 is a perspective view, with parts separated, of the tissue marking apparatus of FIG. 6.

As seen in particular in FIG. 8, tissue marking apparatus 300 includes a push rod 324 disposed within an outer tube 312, immediately proximal of a tissue marker 116 (as described above), to facilitate deployment of marker 116 from outer tube 312. Handle 310 houses a firing mechanism 332 adapted to rapidly deploy tissue marker 116 from the distal end of outer tube 312.

Figure 8A:
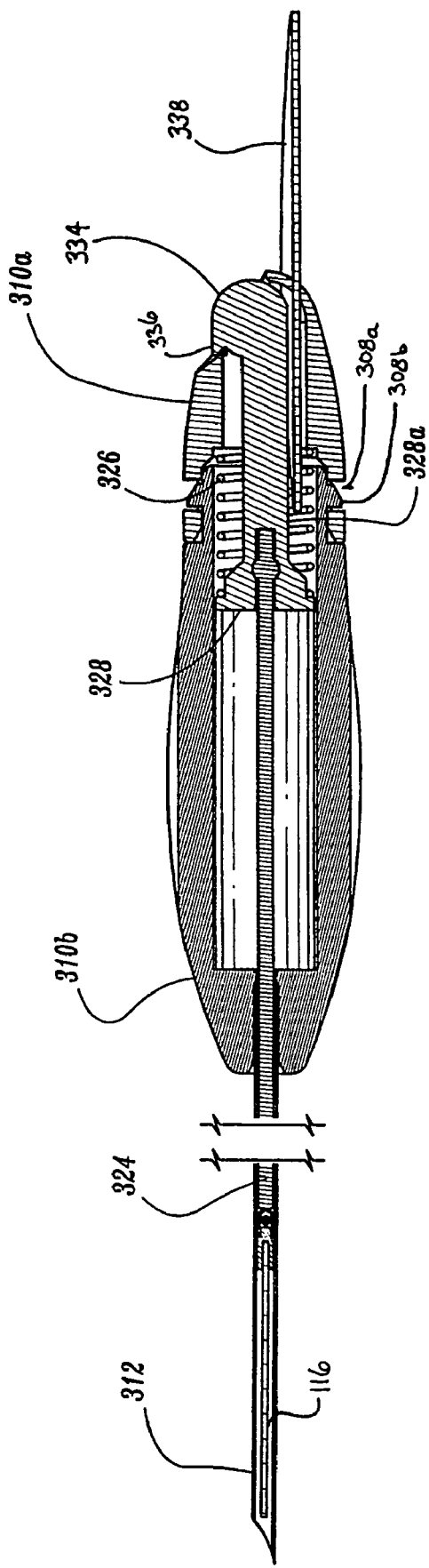
FIG. 8A is a cross-sectional side elevational view, taken along the longitudinal axis, of the tissue marking apparatus of FIG. 5.

Firing mechanism 332 includes, for example, a coil spring 326 configured and dimensioned to be slidably received within distal and proximal tubular portions 310a, 310b. Firing mechanism 332 further includes a firing button 330 having a piston element 328, configured and dimensioned to be received within tubular portion 310b, aproximal end 334, configured and dimensioned to extend through an opening 306 formed in proximal tubular portion 310b, and a shaft portion 328a interconnecting piston element 328 and angled end 334. Piston element 328 is preferably configured and adapted to securely receive a proximal end of push rod 324 in a distal end thereof, as seen in FIG. 8A. Preferably, proximal end 334 of firing button 330 includes a radially projecting lip 336, which lip 336 is configured and dimensioned to engage an edge of opening 306 formed in proximal tubular portion 310a in a snap-fit type engagement. As such, when proximal end 334 extends through opening 306 formed in proximal tubular portion 310a, spring 326 is retained in a compressed state between piston element 328 and an inner surface of proximal tubular portion 310a, as seen in FIG. 8A.

As seen in FIGS. 6-8A, a safety tab 338 is shown inserted through proximal opening 306, between proximal end 334 and tubular portion 310a, in order to wedge lip 336 against the edge of opening 306 and to prevent unintentional firing of marking apparatus 300. Preferably, safety tab 338 is made of a pliable material, such as plastic, which conforms to the contours of opening 306 and proximal end 334. Prior to firing tissue marking apparatus 300, safety tab 338 must be removed from between tubular portion 310a and proximal end 334 in order to permit disengagement of lip 336 from the edge of opening 306.

After removal of safety tab 338, depressing proximal end 334 causes lip 336 to disengage from the edge of opening 306 and permits spring 326 to rapidly decompress and press against the proximal surface of piston element 328 which results in consequent distal movement of piston element 328 to urge push rod 324 forward and to force tissue marker 116 out from the distal end of outer tube 312.

In use, a tissue marking apparatus (i.e., either tissue marking apparatus 100, 200 or 300, as described above), with a tissue marker 116 pre-loaded therein, is removed from its sterile packaging (not shown) and the distal end of outer tube 112, 212, 312 is inserted into the desired location of the patient, either by hand (by pushing the distal end of the outer tube into the tissue) or alternatively, by using a positioning apparatus to advance the tip of the tissue marker apparatus to the target tissue area. Visual markers or radiopaque markers, provided on the outer surface of the instrument (not shown), can be used to angularly orient the hoop as desired. Firing button 130, 230, 330 is manipulated to activate firing mechanism 132, 232, 332 to eject tissue marker 116 from the distal end of outer 112, 212, 312 tube and deploy elongate tail 120 into the patient's tissue. Tissue marking apparatus 100, 200, 300 is then pulled out of the patient, leaving tissue marker 116 in place at the target tissue.

Accordingly, subsequent monitoring of the tagged or marked tissue can be repeated by detecting the radioactive energy emitted from radioactive beads 122 enclosed in capsule 118. When all monitoring is complete, marker 116 is removed by biopsying the tissue surrounding marker 116 to remove anchored marker 116 therefrom.

Figure 11:
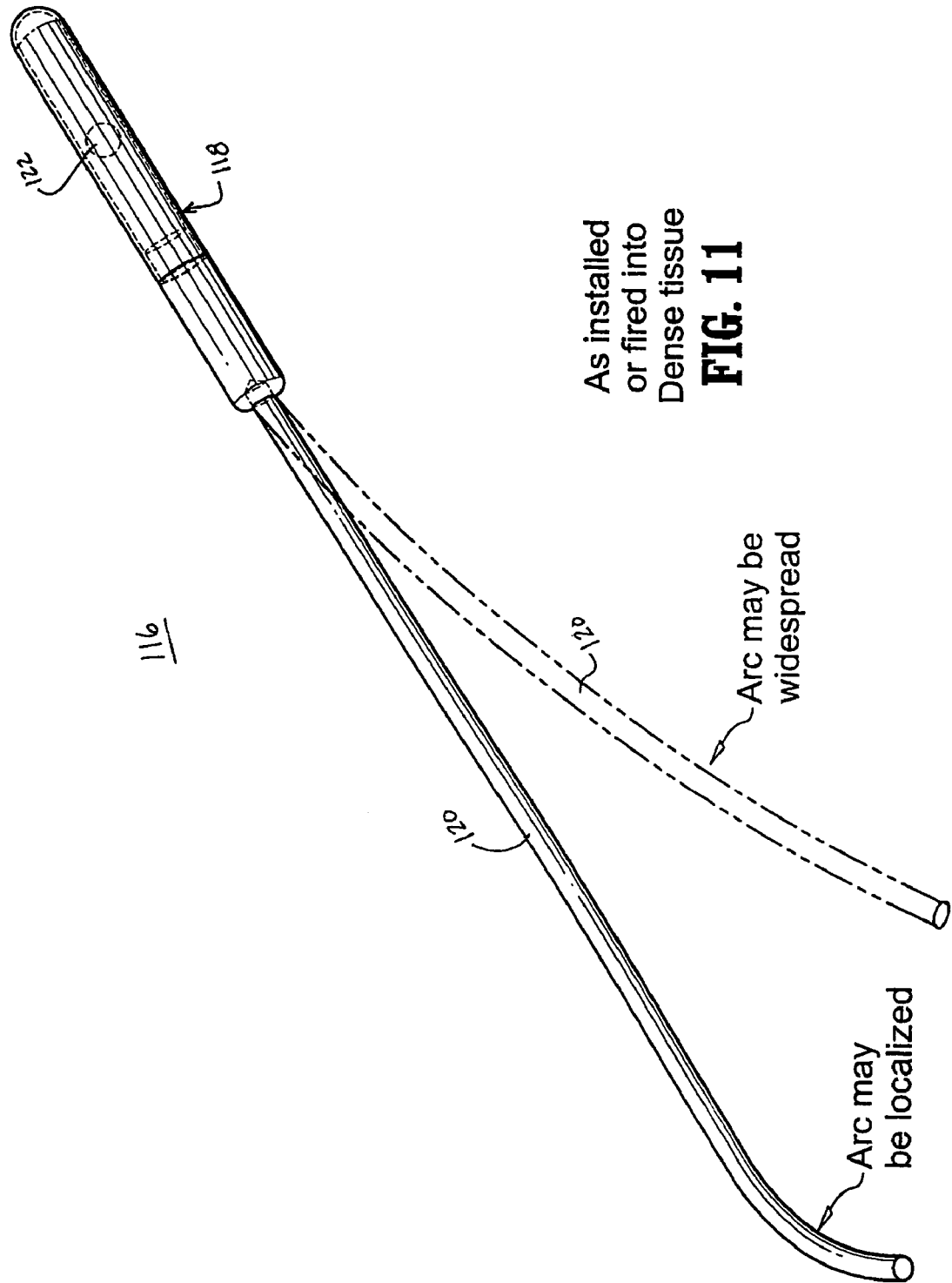
Figure 12:
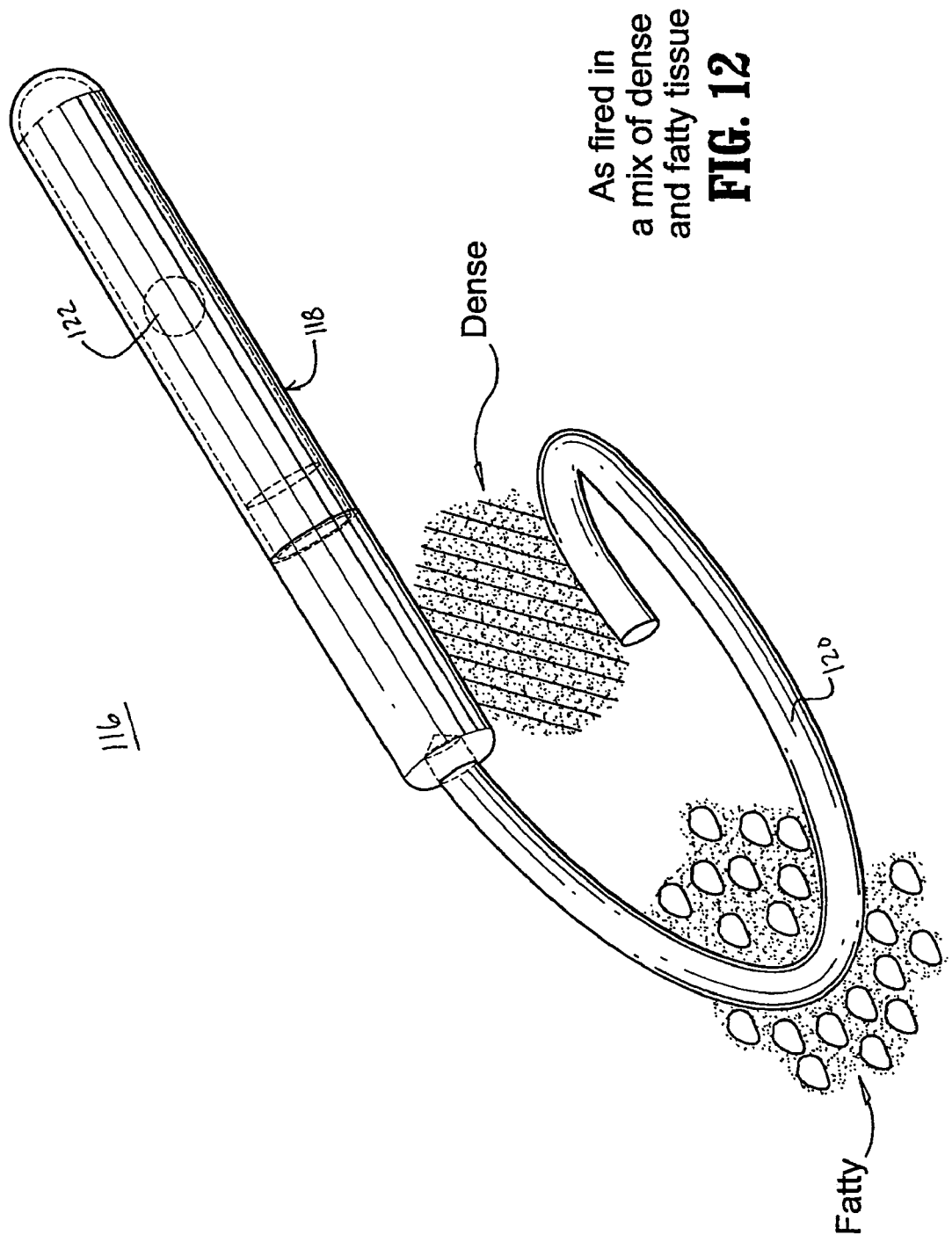
Figure 13:
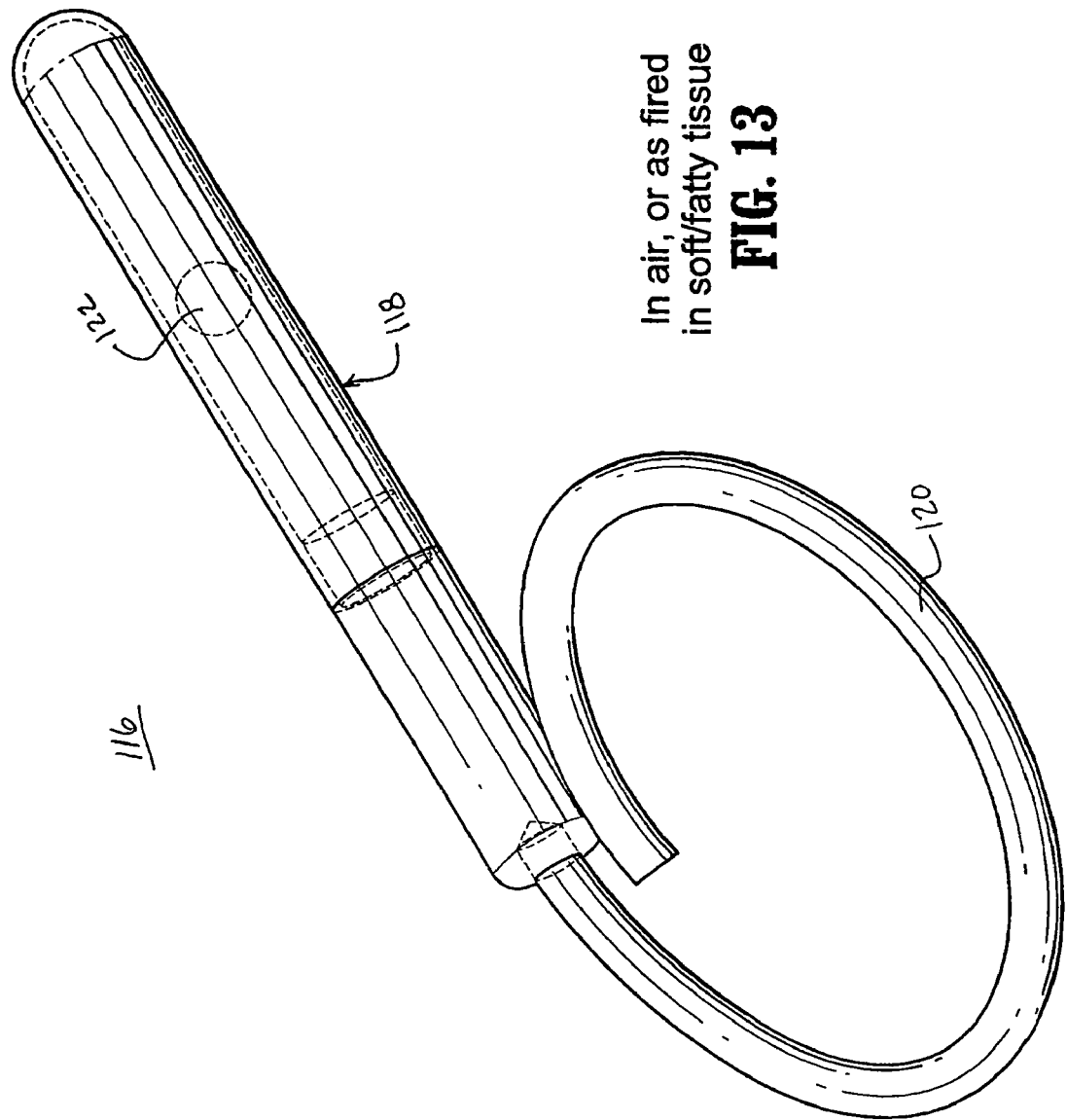

Turning now to FIGS. 9-13, illustrative configurations of flexible elongated tail 120 of tissue marker 116 upon insertion into human, animal or other tissue are shown. In general, denser or more muscular tissue tends to prevent elongated tail 120 from returning to its predetermined shape after being fired into body tissue thereby resulting in a multitude of variations and orientations. In each instance, the elongated tail attempts to achieve its predetermined shape resulting in an "engulfing" motion upon the tissue. The "engulfing" motion prevents the migration of tissue marker 116. The elongate tail 120 takes on a substantially circular or hoop like configuration as illustrated in FIG. 13. It is contemplated that elongate tail 120 can take on many other configurations, including and not limited to, polygonal, ovular and the like. Preferably, elongated tail 120 has a predetermined shape in which the distal tip of elongated tail 120 doubles back and crosses over a region between the median and the proximal end of elongated tail 120.

Figure 9:
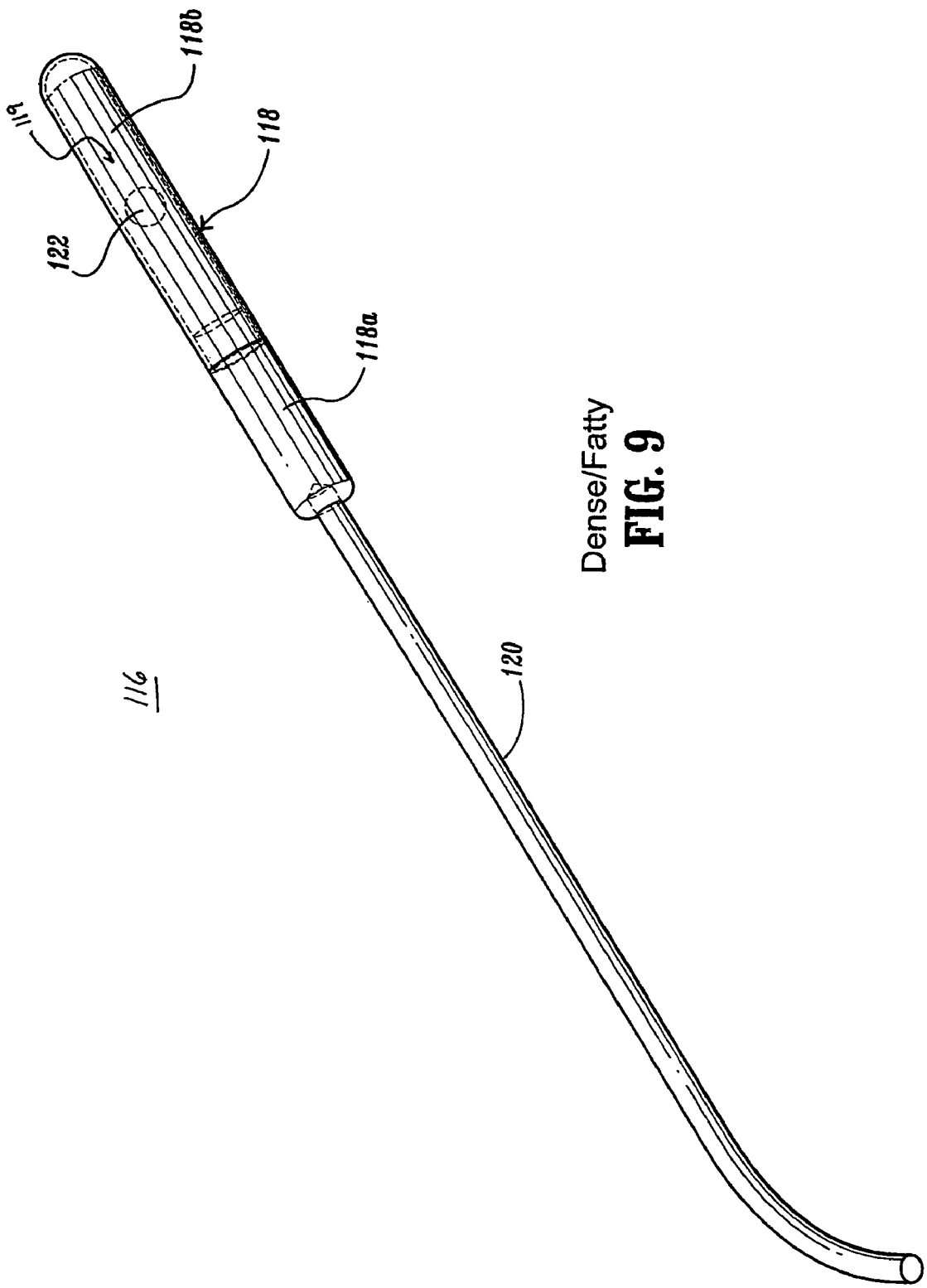
FIGS. 9-13 are enlarged perspective views of an illustrative embodiment of a tissue marker constructed in accordance with the present disclosure, showing various deployment configurations in various types of body tissue.
Figure 10:
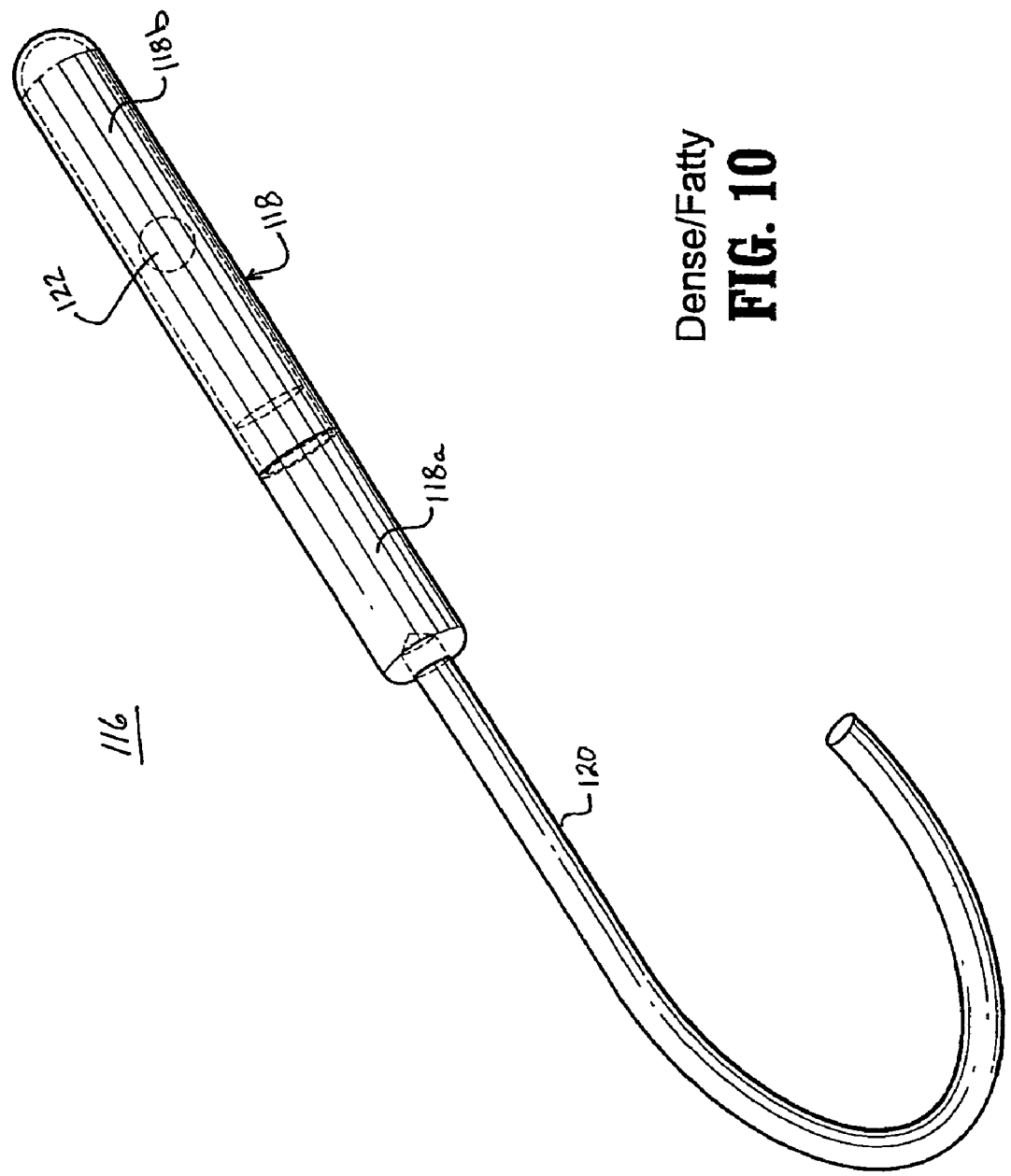

As seen in FIGS. 9 and 10, tissue marker 116 is illustratively shown with elongate tail 120 imbedded within dense/fatty tissue. In FIG. 9, only the distal most end of elongate tail 120 is curved, while in FIG. 10 the median portion and the distal most end of elongate tail 120 are curved. Further, as seen in FIG. 11, when elongate tail 120 is fired into dense tissue, the arc of elongate tail 120 may be localized to the distal most tip or, as seen in phantom, the arc of elongate tail may be widespread of the entire length. As seen in FIG. 12, when elongate tail 120 is fired into a combination of dense and fatty tissue, the median portion of elongate tail 120 has a larger radius of curvature as it passes through fatty tissue, while the distal most end of elongate tail 120 has a smaller radius of curvature as it penetrates denser tissue.

Although illustrative embodiments of the present disclosure have been described herein with reference to the accompanying drawings, it is understood that the disclosure is not limited to those precise embodiments and that various other changes and modifications may be affected therein by one skilled in the art without departing from the scope or spirit of the disclosure. All such changes and modifications are intended to be included within the scope of the present disclosure.

What is claimed is:

1. A tissue marking apparatus for marking a tissue mass of interest within the body of a patient, the tissue marking apparatus comprising:
   a handle;
   a tube operatively coupled to a distal end of the handle;
   a push rod disposed within the tube and extending into the handle;
   a firing mechanism retained within the handle and operatively coupled to a proximal end of the push rod, the firing mechanism being configured and adapted to store a potential energy and upon activation thereof to release said stored potential energy to distally advance the push rod through the tube, the potential energy source configured and adapted to rapidly drive the push rod distally through the tube upon an activation of the firing mechanism, the firing mechanism comprising:

a compression spring slidably retained within the handle; and a firing button slidably retained within the handle, the firing button including:

a distal end defining a piston;

a proximal end defining a lip configured and adapted to engage an edge of an opening formed in a proximal end of the handle; and a shaft portion interconnecting the distal and proximal ends of the firing button, wherein the shaft portion and the proximal end of the firing button extend through the compression spring such that the compression spring is disposed between the piston and the proximal end of the handle, and wherein the compression spring is maintained in a compressed condition when the lip of the firing button is engaged with the edge of the opening formed in the proximal end of the handle; and a marker configured and dimensioned to be slidably received within the tube at a location distal of the push rod;

a capsule defining a chamber therein;

an elongate tail extending from a distal end thereof, the tail having a shape, while in an at rest condition, in which a distal end of the elongate tail approaches a median portion of the elongate tail, the elongate tail being deformable to a substantially linear condition; and at least one radioactive bead retained within the chamber of the capsule.

2. The tissue marking apparatus according to claim 1, wherein the tissue marking apparatus further comprises:

a locking tab configured and adapted to prevent the manipulation of the firing mechanism.

3. The tissue marking apparatus according to claim 2, wherein the locking tab is insertable within the opening formed in the proximal end of the handle, between the proximal end of the firing button and a lower edge of the opening formed in the proximal end of the handle, whereby the locking tab prevents the lip at the proximal end of the firing button from disengaging from the edge of the opening formed in the proximal end of the handle.

4. The tissue marking apparatus according to claim 1, wherein the marker is positioned within the tube such that the elongate tail is distally oriented and the capsule is in contact with the push rod.

5. The tissue marking apparatus according to claim 1, wherein the handle of the tissue marking apparatus comprises:

a distal body portion from which the tube extends; and a proximal body portion, and distal and proximal body portions being configured and adapted to be coupled to one another.

* * * * *